United States Patent [19]

Liner

[11] 4,125,436
[45] Nov. 14, 1978

[54] SLIPS FOR SPECIMEN GROWTH AND MICROSCOPIC EXAMINATION

[75] Inventor: John Liner, Stratford, Conn.

[73] Assignee: Linbro Scientific, Inc., Hamden, Conn.

[21] Appl. No.: 827,457

[22] Filed: Aug. 25, 1977

[51] Int. Cl.² ............................................. C12K 1/10
[52] U.S. Cl. .................................................. 195/127
[58] Field of Search ................... 195/127, 139; 424/3

[56] References Cited

U.S. PATENT DOCUMENTS 2,783,180   2/1957   Whitehead ........................... 424/3 X Primary Examiner—Raymond N. Jones
Assistant Examiner—Robert J. Warden
Attorney, Agent, or Firm—Walter Spruegel

[57] ABSTRACT

A flat transparent slip is formed with an integral handle part, including a prong that rises from the slip and has with the latter outside the confines of a growth area thereon a joint with a constriction for ready snap-off of the handle part from the slip. In another form, a number of slips are arranged in a cluster with an integral handle and so that any slip may be snapped off the handle.

6 Claims, 7 Drawing Figures

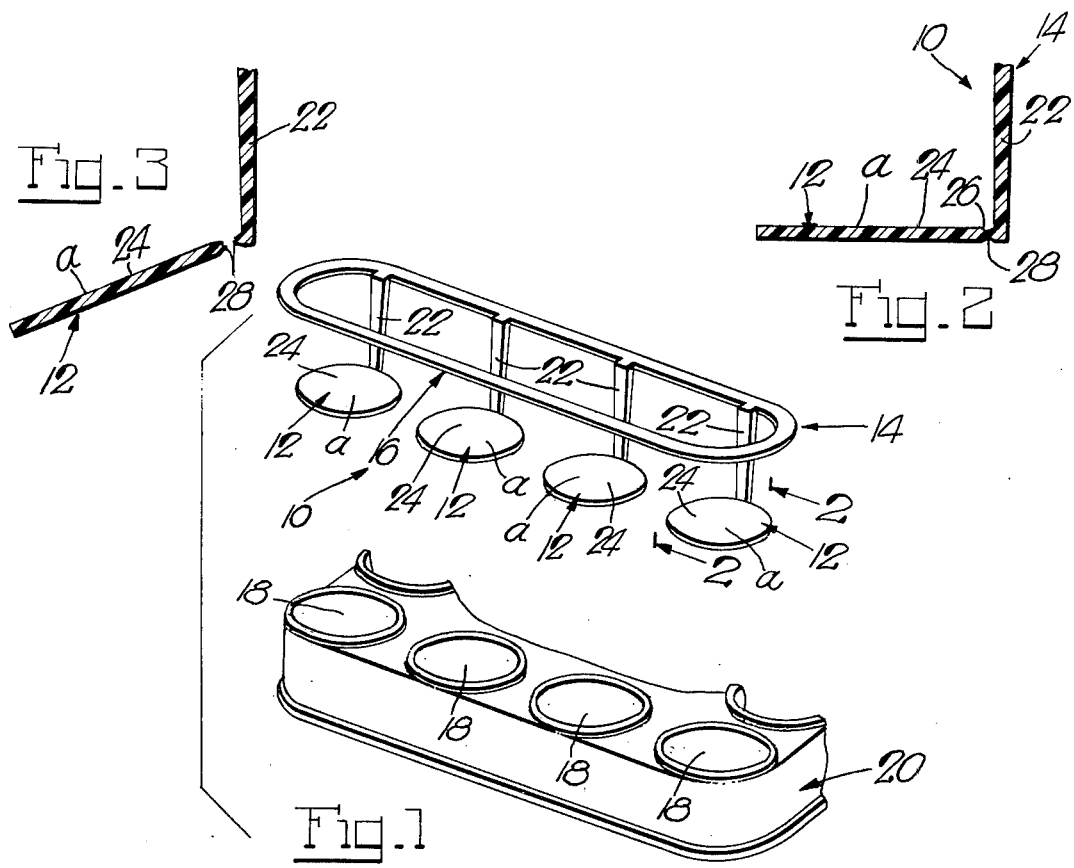
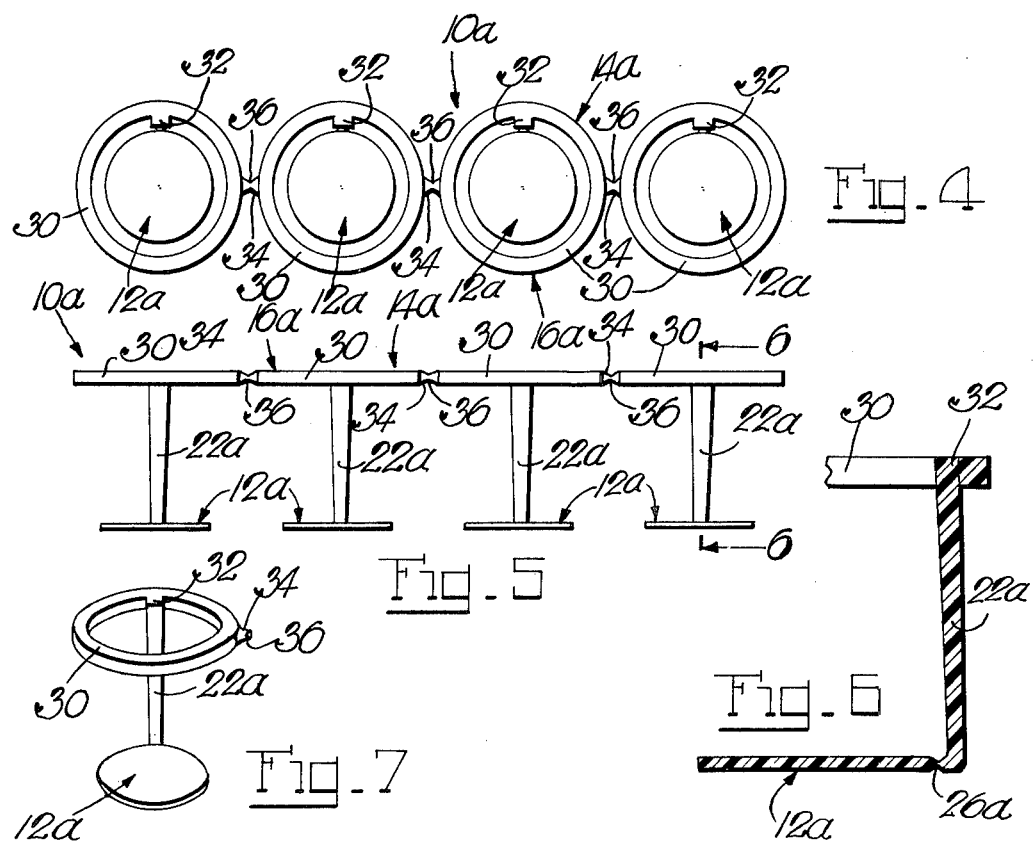

SLIPS FOR SPECIMEN GROWTH AND MICROSCOPIC EXAMINATION

This invention relates to specimen plates in general, and to slips for specimen growth and microscopic examination in paticular.

Slips are thin transparent discs of glass or plastic which are widely used in laboratory procedures involving growth and microscopic examination of specimens. Thus, slips are used for growth thereon of many different specimens, such as cells, bacteria and fungi, for example, with the slips being to this end placed in wells containing media which promote specimen growth. Once sufficient specimens have been grown on a slip, the latter is removed from the well and is then fixed and stained, whereupon the slip is ready for placement under a microscope for examination of the specimens thereon.

While such slips are quite satisfactory in most respects, they are also deficient in a few respects. Thus, with these slips being kept rather small in size for possible advantageous use with molded plates with typical cup formations that serve as wells for the growth media, deposit of the slips in and their removal from such cup formations in safe fashion, i.e., with the specimens intact, is a rather tedious task in any event, and mostly involves careful use of forceps. Further, and also owing to their small size, the task of handling such slips for fixing and staining is as tedious as the task of placing them into and removing them from wells with growth media, and also involves mostly careful use of forceps. The task of thus handling slips with forceps for their deposit in and removal from wells with growth media as well as for their subsequent fixing and staining, becomes particularly cumbersome and tiring in laboratory assignments involving more extensive batchtype specimen growth and examination.

It is a primary object of the present invention to provide slips of any, and even the smallest, size each of which lends itself to ready and effortless handling with a technician's bare fingers for its safe deposit in and removal from a growth medium in a well, including a cup formation in a molded plate, as well as for fixing and staining it. To this end, each slip is molded and formed with a distant handle for ready grasp by the fingers of a technician with the slip in his or her full view, for easily and safely lowering the slip into and raising it from a well with a growth medium and for fixing and staining it, with the joint between the handle and slip being at the periphery of the latter and locally idented for ready and controlled snap-off of the slip from the handle without any damage to the slip that might interfere with the best possible microscopic examination of specimens thereon.

It is another object of the present invention to provide slips in molded cluster form, of which the slips of each cluster lend themselves, for simultaneous growth of specimens on any or all slips, to simultaneous deposit in and removal from cup formations in a molded plate of which the cup formations conform to a standard pattern in their arrangement in transverse rows and equal spacing in each row. To that end, the slips in each cluster are arranged in a row and spaced the same as cup formations in a plate, and the slips are joined by an integral gridwork which also serves as a ready and convenient handle for a technician's fingers for handling the slips, including lowering and raising them into and from cup formations in a plate as well as tilting them for run-off of remaining liquid growth media following their removal from the cup formations and preceding their fixing and staining, with the slips in each cluster being also arranged for ready snapoff from the gridwork for microscope examination of the specimens on each individual slip.

It is a further object of the present invention to provide slips in molded cluster form as aforementioned, of which the slip-connecting gridwork is arranged in sections associated with, and formed as convenient handles for, the respective slips, with these grid sections being further arranged for ready snap-off from each other as well as from their respective slips to thereby obtain, if desired, an individual slip or slips each with or without a handle.

Further objects and advantages will appear to those skilled in the art from the following, considered in conjunction with the accompanying drawings.

In the accompanying drawings, in which certain modes of carrying out the present invention are shown for illustrative purposes:

FIG. 1 is a perspective view of a plate cluster of the invention in association with wells in a molded plate for specimen growth;

FIG. 2 is an enlarged fragmentary section through the plate cluster as taken on the line 2—2 of FIG. 1 and showing a part of the cluster;

FIG. 3 is a section similar to FIG. 2 but showing the part of the cluster broken apart;

FIGS. 4 and 5 are top and front views, respectively, of a plate cluster embodying the invention in a modified manner;

FIG. 6 is an enlarged fragmentary section through the modified plate cluster taken substantially on the line 6—6 of FIG. 5; and FIG. 7 is a perspective view of a part snapped-off from the modified plate cluster of FIGS. 4 and 5.

Referring to the drawings, and more particularly to FIG. 1 and 2 thereof, the reference numeral 10 designates a plate cluster for specimen growth and microscopic examination, providing a plurality of slips 12 and a gridwork 14 which joins the slips 12 and provides a convenient handle 16 for the latter. The plate cluster 10 is preferably and conveniently molded of transparent plastic, with the slips being typical thin discs for growth of specimens thereon when immersed in growth media in any suitable wells 18. The wells 18 are in this instance cup formations in a molded laboratory plate 20 in which the cup formations are arranged in a standard pattern in their disposition in transverse rows and equal spacing from each other, and the slips 12 of the plate cluster are in this instance arranged for simultaneous placement in and removal from the cup formations so as to permit simultaneous batch-type growth of specimens on any or all slips if desired. To this end, the gridwork 14 of the plate cluster 10 holds the slips 12 in coplanar disposition in a row and at a spacing the same as cup formations 18 in the plate 20.

The gridwork 14 of the plate cluster 10 is arranged so that it will not interfere with the cup formations 18 in the plate 20 on lowering the slips 12 into the cup formations 18 all the way to the bottoms thereof, and will leave the slips 12 exposed to the full view of a technician when grasping the handle 16 of the cluster with his or her fingers for manipulating the slips, including lowering and raising them into and from the cup formations 18 in the plate. To this end, the gridwork 14 of the plate cluster 10 includes upright posts or prong 22 on the respective slips 12, and more particularly on the peripheries of the latter so as to be outside the confines of specimen growth areas a on the top faces 24 of the slips, and the handle 16 of the cluster is formed at the top ends of the prong 22 and is thus kept adequately spaced from the slips 12 to permit a technician to manipulate the cluster at the handle 16 with his or her fingers while keeping the slips in full view. The handle part 16 of the gridwork 14 is in this instance of elongated oval ring form.

Provisions are also made for ready snap-off of any slip 12 from the gridwork for accustomed flat placement of such slip onto the stage of a microscope for examination of the specimens on the slip. To this end, each prong 22 is formed in its peripheral joint 26 with the associated slip 12 with a constriction 28 (FIG. 2) which leaves the joint 26, on the one hand sufficiently strong for non-breakoff of the slips from the gridwork in ordinary handling of the cluster, and on the other hand sufficiently weak for ready and controlled snap-off thereat of the slip from the prong with little effort by a technician (FIG. 3), with the break in the joint 26 being within the thickness of the slip and, hence, in no wise interfering with proper flat disposition of the slip on the stage of a microscope for accurate examination of specimens on the slip.

In use of the plate cluster 10, any or all top faces of the slips are prepared for growth of sample specimens thereon, whereupon the cluster is by a technician lowered with the slips 12 into the cup formations 18 of a plate which are charged with suitable growth media. Once sufficient specimens have been grown on the slips, the plate cluster is raised by the technician for removal of the slips from the cup formations in the plate, with the plate cluster being also tilted for run-off of any remaining growth medium from the slips. The specimens on the slips 12 are next fixed and stained preferably while still attached to the gridwork 14. However, the slips 12 will have to be snapped from the gridwork 14 for examination of their specimens under a microscope. While the plate cluster 10 is particularly advantageous for simultaneous batch-type growth of specimens on any or all slips in cup formations in molded laboratory plates, the plate cluster can, of course, be used for specimen growth on any slip or slips 12 in individual wells other than cup formations in plates, with any slip 12 being snapped off the gridwork 14 at any convenient stage of the procedure and in any event prior to microscopic examination of the specimens thereon.

Reference is now had to FIGS. 4 to 6 which show a modified plate cluster 10a that is similar to the described plate cluster 10 of FIG. 1, except that the gridwork 14a provides a handle 16a which is for use for the entire cluster and can also be snapped apart into individual handles 30 for the respective slips 12a. These individual handles 30 are in this instance in the form of rings which at 32 are joined to the top ends of the prongs 22a. Successive ones of these individual handles 30 are also joined at 34, with each of these joints 34 having a constriction 36 for ready snap-off thereat of any handle 30 with its associated slip 12a from a succeeding handle 30 with its associated slip 12a. Thus, the plate cluster 10a can be used, the same as the plate cluster 10 of FIG. 1, as a single unit for simultaneous batch-type growth of specimens on any or all slips 12a, whereupon the slips can be snapped off the cluster for microscopic examination of the specimens thereon, with the slips being so that end snapped off at their constricted joints 26a with the prongs 22a (FIG. 6). The plate cluster 10a may also be snapped apart at the constricted joints 34 between successive handles 30 thereof to provide single slips 12a each with an attached handle 30 (FIG. 7) for processing in a single well for specimen growth and for microscopic examination of the specimens on the slip after snapping the same off its handle.

What is claimed is:

1. A specimen growth and examination plate, comprising a flat transparent plastic slip part with a periphery, and a plastic handle part formed integrally with said slip part and providing a prong with opposite ends and disposed upright with respect to said slip part, a handle at one end of said prong, and a joint connecting the other end of said prong with the periphery of said slip part, with said joint having a constriction for ready snap-off of said slip part from said handle part.

2. A specimen growth and examination plate as in claim 1, in which said handle is in the form of a ring at said one end of said prong.

3. A specimen growth and examination plate cluster, comprising a plurality of flat transparent plastic slip parts each having a periphery, and a plastic handle part formed integrally with said slip parts and holding the latter equally spaced in a row and disposed in a common plane, with said handle part including prongs having opposite ends and being disposed upright on said plane and with one end thereof closely spaced from the peripheries of the respective slip parts, and a joint connecting said one end of each prong with the closely spaced periphery of the respective slip part and having a constriction for ready snap-off of said slip part from said handle part.

4. A specimen growth and examination plate cluster as in claim 3, in which said handle part further includes a plastic oval ring in a plane parallel to said common plane and joined with said prongs at the other ends thereof.

5. A specimen growth plate cluster as in claim 3, in which said handle part further includes successive handle sections associated with successive slip parts in the row and with the prongs extending therefrom, and joints between successive handle sections with constrictions for ready snap-off of any handle section with its associated slip from a succeeding handle section with its associated slip.

6. A specimen growth plate cluster as in claim 5, in which said handle sections are ring formations at the other ends of the associated prongs.

* * * * *